United States Patent
Saito et al.

(10) Patent No.: US 7,618,586 B2
(45) Date of Patent: Nov. 17, 2009

(54) AUTOMATIC BLOOD CHEMISTRY ANALYZER

(75) Inventors: Yoshiaki Saito, Hitachinaka (JP); Kazuhiro Nakamura, Naka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 388 days.

(21) Appl. No.: 11/302,342

(22) Filed: Dec. 14, 2005

(65) Prior Publication Data
US 2006/0153737 A1   Jul. 13, 2006

(30) Foreign Application Priority Data
Dec. 15, 2004 (JP) ............................. 2004-362165

(51) Int. Cl.
*G01N 35/00* (2006.01)
(52) U.S. Cl. .................. 422/67; 422/106; 422/105; 422/99; 422/50; 436/55; 73/863.01
(58) Field of Classification Search ............... 422/68.1, 422/81, 67, 99, 100, 105, 106; 436/55; 73/863.01
See application file for complete search history.

(56) References Cited

U.S. PATENT DOCUMENTS 5,880,364 A    3/1999   Dam
5,885,530 A *  3/1999   Babson et al. ............... 422/65
5,939,326 A *  8/1999   Chupp et al. ................ 436/43

FOREIGN PATENT DOCUMENTS

| EP | 0403905    | 12/1990 |
| JP | 59065768   | 4/1984  |
| JP | 02-195259  | 8/1990  |
| JP | 08-278313  | 10/1996 |
| JP | 09-257804  | 10/1997 |
| JP | 11-094841  | 4/1999  |

* cited by examiner

*Primary Examiner*—Jill Warden
*Assistant Examiner*—Cedric Chan
(74) *Attorney, Agent, or Firm*—Mattingly & Malur, P.C.

(57) ABSTRACT

An automatic analyzer for performing qualitative and quantitative analyses of living samples, such as blood and urine, which effectively utilizes the sample and enables requested tests to be performed as many as possible, when sample deficiency is predicted as a result of measuring a sample volume in advance. The analyzer includes a unit for measuring a sample volume, and has a function of, when sample deficiency is predicted, automatically changing an analysis mode to a decrease sample assay for a part of tests, thereby reducing a sample volume required depending on the measured sample volume.

4 Claims, 5 Drawing Sheets

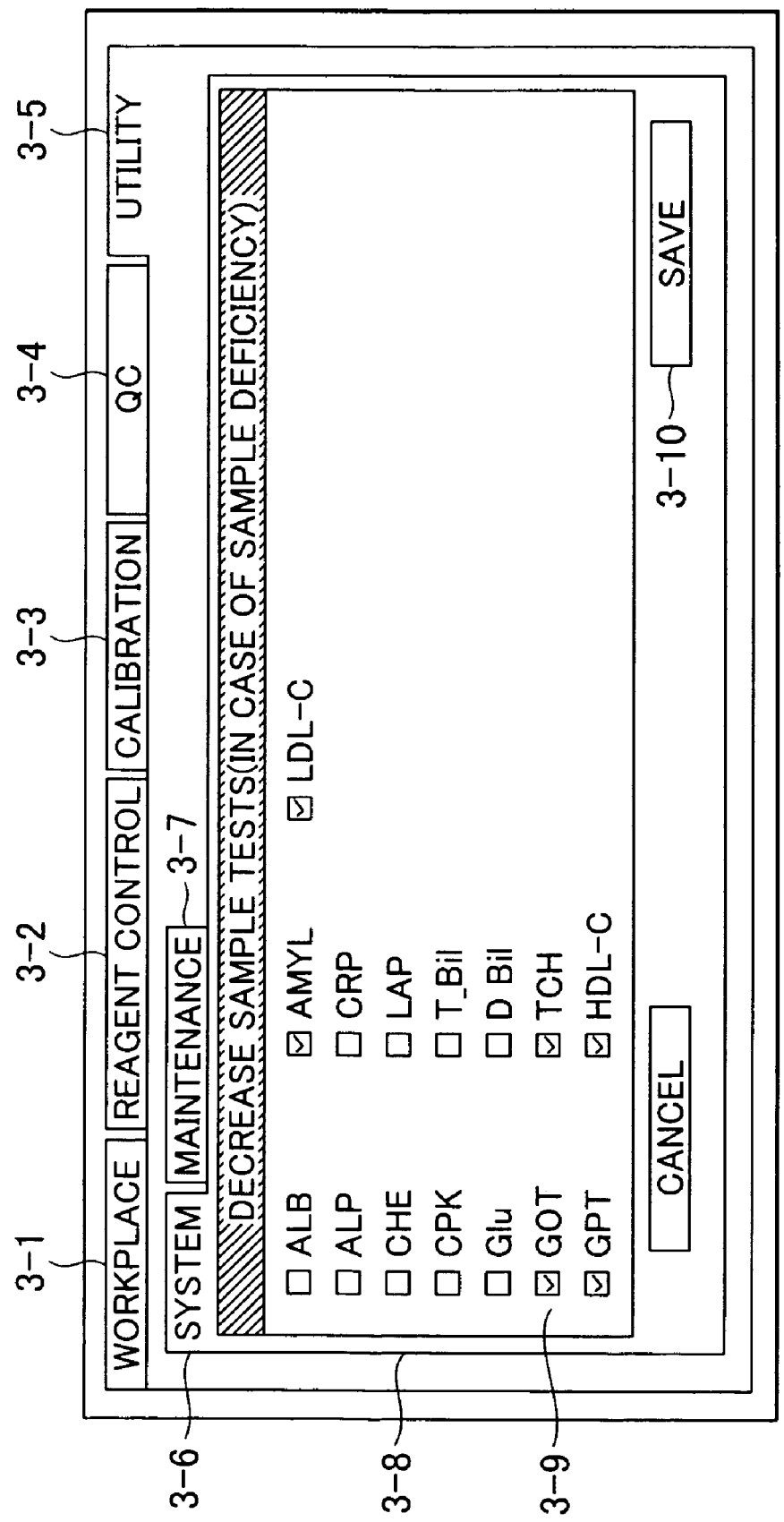

FIG. 4

TEST PRIORITY ORDER

ANALYSIS MODULE [ C ]
PRIORITY RULE [ ANALYSIS TIME ORDER ▼ ] ~4-2

| TEST CODE ORDER |
| ASCENDING ORDER OF USED SAMPLE AMOUNT |
| DESCENDING ORDER OF ANALYSIS TIME |
| USER SETTING |

PRIORITY ORDER TEST NAME

| | |
|---|---|
| 1 | Glu |
| 2 | GOT |
| 3 | GPT |
| 4 | ALP |
| 5 | T-Bil |
| 6 | CHE |
| 7 | ALB |
| 8 | D-Bil |
| 9 | AMYL |
| 10 | CPK |
| 11 | LDL-C |
| 12 | HDL-C |
| 13 | TCH |
| 14 | CRP |

▲ ~4-4
▼ ~4-5

[ CANCEL ]   [ SAVE ] ~4-6

FIG. 5

DECREASE SAMPLE TEST SETTING IN CASE OF SAMPLE DEFICIENCY

5-1 — ○ ALL SAMPLES
5-2 — ◉ PARTIAL SAMPLE (S)

☑ SMALL QUANTITY SAMPLE
☐ RERUN SAMPLE
☐ USER SETTING

AUTOMATIC BLOOD CHEMISTRY ANALYZER

BACKGROUND OF THE INVENTION

1. Field of the Invention

The present invention relates to an automatic analyzer for performing qualitative and quantitative analyses of living samples, such as blood and urine, and more particularly to a multi-test automatic analyzer capable of analyzing the same sample on a plurality of analysis tests.

2. Description of the Related Art

In an automatic analyzer, when a plurality of analysis tests are requested for one patient sample, the patient sample is divided into small volumes (child samples are pipetted from a parent sample), and respective analyses are performed in a particular order, e.g., in a test registration order. However, when the sample volume is small, such as a sample of a child patient, it sometimes happens that the sample is exhausted prior to performing the analysis on a test important for diagnosis, and the requested analysis tests cannot be completely finished. One proposed solution is to make higher priority in analysis order settable to the test important for diagnosis so that the important test can be surely performed even when the sample volume is small.

Patent Reference 1 (JP,A 9-257804) discloses an automatic analyzer with the function of pipetting a sample and performing analyses of the pipetted samples in accordance with the analysis priority order, which has been set by an operator in advance, when the sample volume in a sample tube is not larger than a certain value.

SUMMARY OF THE INVENTION

Even the automatic analyzer disclosed in Patent Reference 1 accompanies with a risk that, when the sample volume is small and there are a plurality of tests important for diagnosis, the sample is exhausted before the desired analysis result is obtained.

An object of the present invention is to provide an automatic blood chemistry analyzer capable of performing requested tests as many as possible even when the sample volume is small.

To achieve the above object, the automatic blood chemistry analyzer of the present invention includes a unit for measuring a sample volume, and has a function of, when sample deficiency is predicted, automatically changing an analysis mode to a decrease sample assay for a part of tests, thereby reducing a sample volume required (sample pipetting volume) depending on the measured sample volume.

According to the present invention, even when the sample volume is not sufficient to perform all of requested tests, the number of measurable tests can be increased by automatically changing the analysis mode to the decrease sample assay for one or more predetermined tests.

BRIEF DESCRIPTION OF THE DRAWINGS

FIG. 3 shows one example of a decrease sample test setting screen;

FIG. 4 shows one example of a test priority order setting screen;

FIG. 5 shows one example of a decrease sample test setting screen when the sample volume is insufficient.

DESCRIPTION OF THE PREFERRED EMBODIMENTS

An embodiment of the present invention will be described below with reference to the attached drawings.

Figure 2:
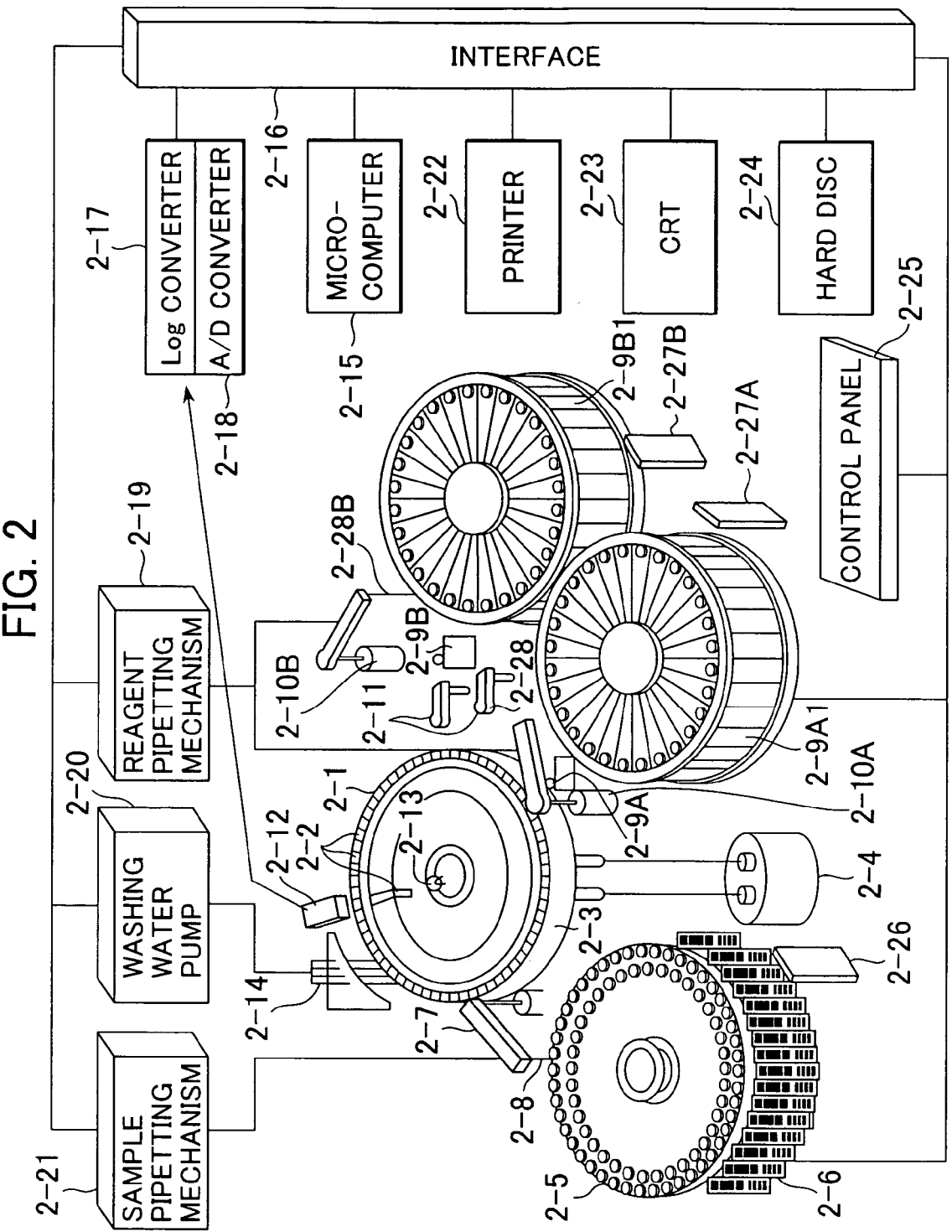
FIG. 2 is a schematic view of the automatic blood chemistry analyzer according to the embodiment of the present invention.

FIG. 2 schematically shows a basic arrangement of an automatic blood chemistry analyzer according to the embodiment of the present invention. In FIG. 2, reference numeral 2-1 denotes a reaction disc. Reaction cuvettes 2-2 are placed on an outer peripheral portion of the reaction disc 2-1. The whole of the reaction disc 2-1 is held at a predetermined temperature by a reaction disc incubator 2-3.

Reference numeral 2-5 denotes a sample disc mechanism on which many test tubes containing samples and having barcodes 2-6 affixed thereto are placed. The sample in each test tube affixed with the barcode 2-6 is extracted, as required, by a nozzle 2-8 of a sample pipetter 2-7, and is poured into the reaction cuvette 2-2 placed in a sample pipetting position. Reference numerals 2-9A1, 2-9B1 denote reagent disc mechanisms on which reagent bottles each affixed with a barcode label are placed. Barcode readers 2-27A, 2-27B are associated with the reagent disc mechanisms 2-9A1, 2-9B1, respectively. At the time of registering reagents, reagent bottle information is registered corresponding to the reagent bottles placed in the barcode read positions. A second reagent pipetter 2-10A and a first reagent pipetter 2-10B are installed near the reagent disc mechanisms 2-9A1, 2-9B1, respectively. Stirrers 2-11 are also installed near the reagent disc mechanisms 2-9A1, 2-9B1. Reference numeral 2-12 denotes a multi-wavelength spectrometer, and 2-13 denotes a light source. The reaction cuvette 2-2 containing a photometric target is positioned between the multi-wavelength spectrometer 2-12 and the light source 2-13. Reference numeral 2-14 denotes a washing unit. A control unit and a signal processing unit include a microcomputer 2-15, an interface 2-16, a Log converter 2-17, and an A/D converter 2-18. Further, reference numeral 2-19 denotes a reagent pipetting mechanism, 2-20 denotes a washing water pump, and 2-21 denotes a sample pipetting mechanism. In addition, the control unit includes a printer 2-22 for printing data, a CRT 2-23 for display, a hard disc 2-24 serving as a memory, and a control panel 2-25 (e.g., a keyboard or a pointing device such as a touch screen or a mouse) for entry of information.

In FIG. 2, the sample put in the test tube affixed with the barcode is pipetted in predetermined volume into the reaction cuvette 2-2 by using the nozzle 2-8 of the sample pipetter 2-7 in accordance with analysis parameters which have been previously inputted through the control panel and stored in a memory within the microcomputer 2-15.

Then, the reaction cuvette 2-2 containing the pipetted sample is moved to the reagent pipetting position by rotating the reaction disc 2-1. Thereafter, reagents are pipetted in predetermined volumes into the reaction cuvette 2-2 containing the pipetted sample by using respective nozzles of the reagent pipetters 2-10A, 2-10B in accordance with the analysis parameters which have been previously inputted through the control panel and stored in the memory within the microcomputer 2-15.

Then, the sample and the reagents are stirred and mixed with each other by using the stirrers 2-11.

When the relevant reaction cuvette 2-2 moves across the photometric position, the absorbance of the sample is measured by the multi-wavelength spectrometer 2-12. The measured absorbance is taken into the microcomputer 2-15 via the Log converter 2-17, the A/D converter 2-18, and the interface 2-16. The absorbance is converted to concentration data in accordance with a working curve obtained from the absorbance of a calibrator, which has been previously measured by a designated analytical method per test. The thus-measured concentration data for each component is outputted to the printer and/or the screen.

In the analysis based on the above-described principle, a user sets various parameters necessary for the analyses, registers the samples, and confirms the analysis result on the screen (CRT) 2-23.

One example of a manner for realizing the present invention will be described in detail below.

Figure 1:
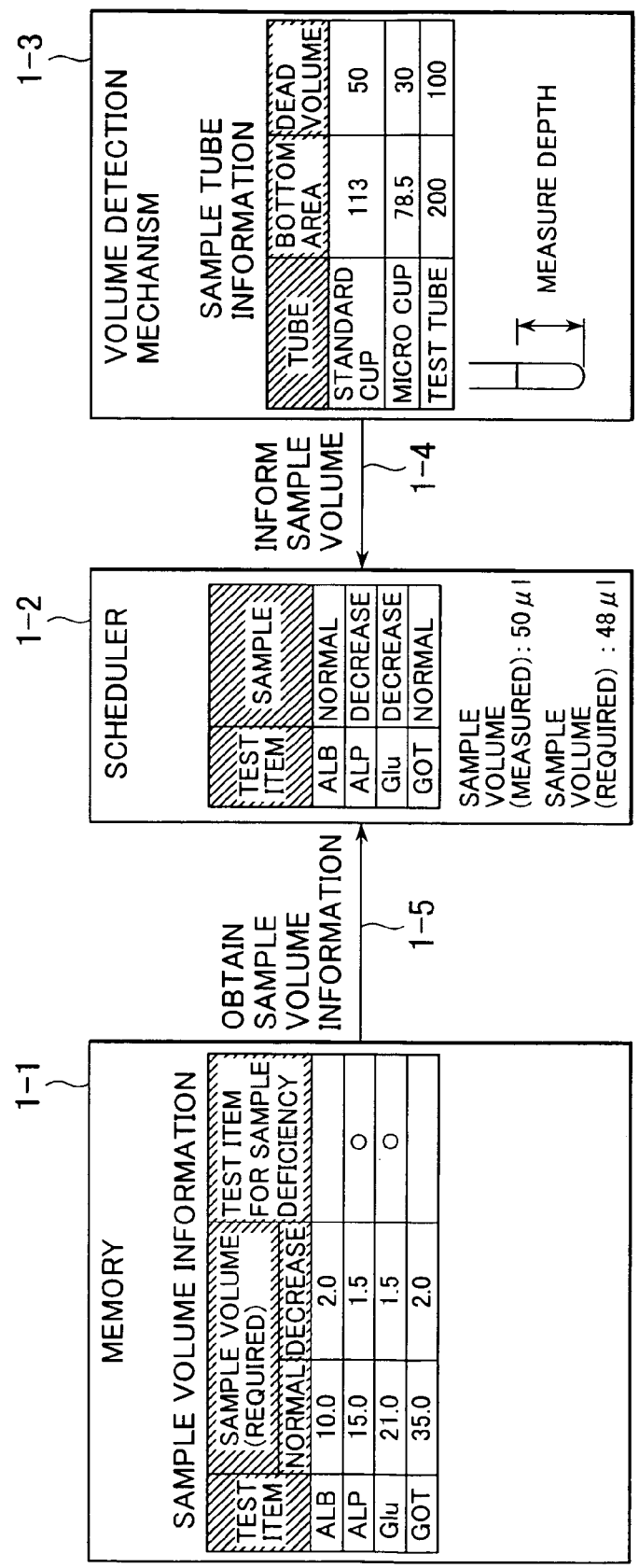
FIG. 1 is a block diagram showing basic overall outlines of an automatic blood chemistry analyzer according to an embodiment of the present invention.

FIG. 1 is a block diagram showing the automatic blood chemistry analyzer according to the embodiment of the present invention.

The analyzer comprises a memory 1-1, a scheduler 1-2, and a volume detection mechanism 1-3.

When a new sample is analyzed, the sample depth in the sample tube is measured by the volume detection mechanism 1-3 in advance. The sample depth can be measured, for example, by means of a sensor or image processing. The volume detection mechanism 1-3 calculates the sample volume based on the measured sample depth and sample tube information. In the case of a tubular sample tube, for example, the sample volume can be calculated using a formula of (bottom area of sample tube)×(sample depth)−(dead volume).

The memory 1-1 includes a sample volume information table storing the sample volume required for each test, and the scheduler 1-2 calculates, based on the sample volume information table, a total normal volume required in tests requested for the relevant sample.

When the total normal volume required in the requested tests is larger than the measured sample volume, the scheduler 1-2 searches for the test, for which a decrease sample assay is to be performed in the case of sample deficiency, based on the sample volume information table in the memory 1-1, and then prepares a schedule so as to perform an analysis on the relevant test by using the decrease sample assay. The decrease sample assay can be applied to some analysis tests, but not applicable to others. Also, the measurement accuracy of the decrease sample assay is lower than that of an ordinary assay. For that reason, it is preferable that, instead of designating the decrease sample assay to be performed on all of the analysis tests adaptable for the decrease sample assay when the sample volume is insufficient, the decrease sample assay is designated to only the analysis test for which the measurement accuracy is not so required in consideration of the symptom of the relevant patient. From this point of view, the analyzer preferably has the function of enabling the user to designate one or more desired tests for which the decrease sample assay is to be performed.

In the example shown in FIG. 1, analysis tests corresponding to ALB, ALP, Glu and GOT are requested. The total normal volume required in the requested tests is 86 μl, but the measured sample volume is 50 μl. If the tests are performed using the respective normal volumes, GOT cannot be analyzed because of sample deficiency. Therefore, the analysis mode is automatically changed to the decrease sample assay for ALP and Glu which can be analyzed by the decrease sample assay. As a result, the total volume required in the requested tests becomes 48 μl and all the requested tests can be performed.

FIG. 3 represents one example embodying the feature of the present invention set forth in claim 2. FIG. 3 shows a screen for selecting the test for which the analysis mode is automatically changed to the decrease sample assay.

The analyzer has the functions of "workplace" 3-1, "reagent" 3-2, "calibration" 3-3, "QC (Quality Control)" 3-4, "utility" 3-5, etc. The utility screen 3-5 includes a "system" 3-6 for making basic setting of the overall system, "maintenance" 3-7 for carrying out maintenance of the analyzer, etc. The system screen 3-6 contains a decrease sample test setting screen 3-8 displaying a list of all tests capable of being requested. Each test item has a means (e.g., check box) 3-9 allowing the user to select whether the analysis mode is changed to the decrease sample assay when the sample volume is insufficient. By depressing a save button 3-10 after entering a check mark in the box, the relevant test is registered in the sample volume information table within the memory 1-1 as a test item for which the decrease sample assay is to be performed in case of sample deficiency.

With reference to FIG. 4, a description is now made of a screen allowing the user to set the priority order of tests performed on one sample when the sample amount is insufficient even after change to the decrease sample assay. A test priority order setting screen 4-1 includes as a priority rule selecting box 4-2 as means capable of easily setting the test priority order in accordance with desired one of priority rules. The priority rules include, for example, a test code order, an ascending order of required sample amount, a descending order of analysis time, and user setting. When the ascending order of required sample amount is selected, the test using a smaller sample volume is performed with higher priority, and therefore the number of tests performable in the case of sample deficiency can be increased in comparison with the normal case. When the descending order of the analysis time is selected, the time required for completing a series of analyses for each sample can be minimized.

Upon selection of one priority rule, the tests registered in the analyzer are displayed in a priority order display area 4-3 in the order according to the selected priority rule. By depressing a save button 4-6, the test order displayed in the priority order display area 4-3 is stored in the memory 1-1 for registration. After the registration, the tests are performed in the stored order.

As one of the priority rules, there is user setting. When the user setting is selected, the user can freely rearrange the test order at the user's discretion in consideration of which test is more important, and the rearranged order can be stored in the memory 1-1. Buttons 4-4, 4-5 are prepared, by way of example, as means for allowing the user to rearrange the test order. When the button 4-4 is depressed after selecting D-Bil in the priority order display area 4-3, for example, the priority order of D-Bil shifts to No. 7 and the priority order of ALB shifts to No. 8. On the other hand, when the button 4-5 is depressed after selecting D-Bil in the priority order display area 4-3, for example, the priority order of D-Bil shifts to No. 9 and the priority order of AMYL shifts to No. 8.

FIG. 5 represents an example embodying one feature of the present invention. FIG. 5 shows a screen for selecting a target for which the analysis mode is automatically changed to the decrease sample assay when the sample volume is insufficient. This setting screen contains means (selectable items) 5-1, 5-2 for allowing the user to select "all samples" or "partial sample(s)" as the target for which the analysis mode is automatically changed to the decrease sample assay when the sample volume is insufficient. The setting screen further contains the function of enabling a small quantity sample in a micro sample tube, a rerun sample, and/or a sample set by the user to be set as the target when "partial sample(s)" is selected. A check box of "small quantity sample" enables the analyzer to operate in a mode of performing only measurable tests with high accuracy or a mode of performing tests as many as possible when the sample deficiency is predicted as in a sample of a child patient. Also, by keeping off a check box of "rerun", setting can be made such that, even when the relevant test is a target of the decrease sample assay, it can be performed with high accuracy using a normal sample volume at the time of rerun.

Figure 6:
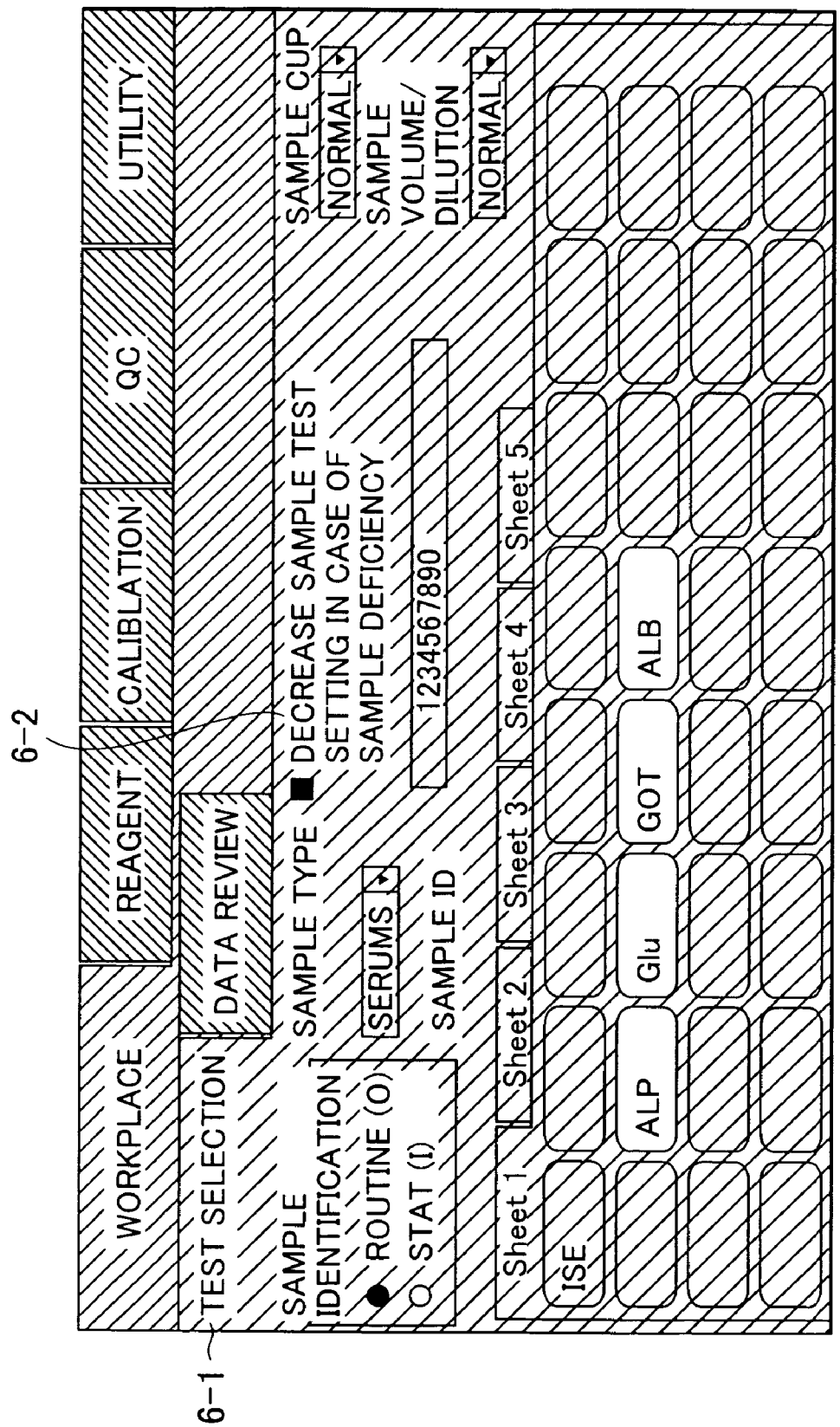
FIG. 6 shows one example of a screen for setting enabling the analysis mode to be automatically changed to a decrease sample assay per sample.

FIG. 6 shows a screen for setting that enables the analysis mode to be automatically changed to the decrease sample assay per sample when "user setting" is selected in the screen of FIG. 5. A test selection screen 6-1 is a screen displaying requested tests per sample and contains means (selection area) 6-2 for selectively setting each test for which the analysis mode is automatically changed to the decrease sample assay when the sample volume is insufficient. Thus, the above setting can be made at the user's discretion in a selective manner.

What is claimed is:

1. An automatic blood chemistry analyzer comprising:
   a sample tube for containing a sample for which sample assays as to plural test items are to be performed;
   a volume detection mechanism for measuring a sample volume in said sample tube;
   a display screen to be used for selecting test items of said plurality of test items for which a sample assay is automatically changed to decrease sample assay;
   a memory for storing normal sample volume information and decrease sample volume information for each of the test items, and for storing the test items for which a sample assay is automatically changed to decrease sample assay;
   a scheduler for calculating a total normal volume required for a sample to be used in a normal sample assay for all of the test items for the sample on the basis of the normal sample volume information stored in said memory, selecting said decrease sample volume information stored in said memory when said sample volume in said sample tube is smaller than said total normal volume required for a sample to be used in a normal sample assay for all of the test items for the sample, and preparing a schedule to perform an analysis test by using said normal sample assay or said decrease sample assay for the test item for which the analysis test is performed, for each test item according to the normal sample volume information and the decrease sample volume information;
   a sample pipette for pipetting a sample into a reaction cuvette in accordance with said schedule prepared by said scheduler;
   means for allowing the user to select whether the decrease sample assay is to be performed for each of tests designated on the display screen in advance, when the decrease sample assay is selected for the part of the tests to which the decrease sample assay is applicable; and
   a selection screen for allowing the user to select whether a target sample is a quantity less than a predetermined minimum quantity sufficient for a normal analysis or a rerun sample, when the decrease sample assay is selected for the part of the tests to which the decrease sample assay is applicable.

2. The automatic blood chemistry analyzer according to claim 1, further comprising means for allowing the user to set on the display screen a priority order of tests performed on one sample, when sample volume is insufficient even if the decrease sample assay is executed on one or more tests designated in advance.

3. The automatic blood chemistry analyzer according to claim 2, further comprising means for allowing the user to select, as said priority order, one of at least a test code order, an ascending order of required sample amount, and a descending order of analysis time.

4. The automatic blood chemistry analyzer according to claim 2, further comprising means for allowing the user to register said priority order in advance.

* * * * *